(12) United States Patent
    Dunca

(10) Patent No.: US 10,772,783 B2
(45) Date of Patent: Sep. 15, 2020

(54) ANKLE REHABILITATION DEVICE

(71) Applicant: Adrian Dunca, Bel Air, MD (US)

(72) Inventor: Adrian Dunca, Bel Air, MD (US)

( * ) Notice: Subject to any disclaimer, the term of this patent is extended or adjusted under 35 U.S.C. 154(b) by 311 days.

(21) Appl. No.: 15/876,607

(22) Filed: Jan. 22, 2018

(65) Prior Publication Data

US 2019/0224031 A1    Jul. 25, 2019

(51) Int. Cl.
*A61H 1/02*    (2006.01)
*A63B 23/08*   (2006.01)

(52) U.S. Cl.
CPC ............ *A61H 1/0266* (2013.01); *A63B 23/08* (2013.01)

(58) Field of Classification Search
CPC .......... A63B 21/023–025; A63B 21/04–0407; A63B 21/0421–0425; A63B 21/045; A63B 21/4013–4015; A63B 21/4034; A63B 2023/003; A63B 23/08–10; A61H 1/0266; A61H 2205/12
See application file for complete search history.

(56) References Cited

U.S. PATENT DOCUMENTS

| | | | |
|---|---|---|---|
| 1,509,793 A * | 9/1924 | Thompson | A63B 21/023 482/79 |
| 1,911,390 A * | 5/1933 | Pullman | A61H 1/0266 482/79 |
| 4,111,416 A * | 9/1978 | Jinotti | A63B 21/023 482/128 |
| 4,186,920 A * | 2/1980 | Fiore | A63B 22/18 403/138 |
| 4,739,986 A * | 4/1988 | Kucharik | A63B 23/08 482/146 |
| 5,035,421 A * | 7/1991 | Scheller | A63B 21/023 482/130 |
| 5,069,445 A * | 12/1991 | Mai | A63B 23/085 482/30 |
| 5,368,536 A * | 11/1994 | Stodgell | A63B 21/00072 482/123 |
| 5,518,476 A * | 5/1996 | McLeon | A63B 23/08 482/79 |
| 6,572,514 B1 * | 6/2003 | Calafato | A63B 22/0056 482/79 |
| 6,780,142 B1 * | 8/2004 | Takizawa | A61H 1/0259 482/70 |
| 6,796,928 B1 * | 9/2004 | Christopher | A63B 22/0056 482/123 |
| 6,821,235 B1 * | 11/2004 | Johnson | A63B 21/0552 482/146 |
| 10,434,357 B2 * | 10/2019 | McCarthy | A63B 21/4047 |
| 2005/0137065 A1 * | 6/2005 | Zoller | A63B 23/08 482/117 |

(Continued)

*Primary Examiner* — Jennifer Robertson

(57) ABSTRACT

A device for rehabilitating or strengthening the ankle includes a plank that is connected by a transversely oriented hinge and a longitudinally oriented pivot, as well as a pair of compression springs at its forward end. The connections of the plank to the underlying base limit the plank to motion in two directions about two axes, thereby providing four types of therapeutic ranges of motion, including dorsiflexion and plantar flexion, eversion and inversion. A transversely slidable foot rest enables the user to hold device 21 in position with one foot while using the plank of the device to rehabilitate the other foot.

20 Claims, 6 Drawing Sheets

(56) References Cited

U.S. PATENT DOCUMENTS

| | | | |
|---|---|---|---|
| 2006/0122040 A1* | 6/2006 | Nguyen | A63B 23/08 |
| | | | 482/80 |
| 2010/0279835 A1* | 11/2010 | Ozawa | A63B 21/00178 |
| | | | 482/142 |
| 2011/0111927 A1* | 5/2011 | Kim | A63B 22/0056 |
| | | | 482/52 |
| 2019/0160322 A1* | 5/2019 | McCarthy | A63B 23/03541 |
| 2020/0086172 A1* | 3/2020 | Tarkington | A63B 21/022 |

\* cited by examiner

ANKLE REHABILITATION DEVICE

FIELD

The present disclosure relates to rehabilitation devices for humans and, in particular to ankle rehabilitation devices.

BACKGROUND

Current rehabilitation devices suffer from various drawbacks and disadvantages. In certain instances, rehabilitation devices are geared more toward building muscle or other gym-type exercises, and are not well suited for rehabilitation of locomotor deficiencies, such as those needed for recovery after stroke, ankle sprain, strain, fracture, or pre- and post-surgery.

It is important for ankle rehabilitation devices to be simple and cost effective, while also being therapeutically beneficial at achieving the desired rehabilitations. Unfortunately, ankle rehabilitation of the current art is often needlessly complex in terms of manufacture and use, and inefficient in terms of addressing rehabilitation and related therapeutic needs of the user.

Accordingly, it would be desirable to address the foregoing drawbacks and disadvantages with a suitable ankle rehabilitation device.

SUMMARY OF THE INVENTION

In one possible implementation, an ankle rehabilitation device is useful for either one of a user's feet. The device has a base platform, which can be oriented so that it has a near or proximal end and a forward or distal end, and the base platform has end portions at each of these ends. A longitudinal axis extends between the end portions. A base platform extends over a width to define opposite sides. A transverse axis is perpendicular to the longitudinal axis and extends between the sides of the base platform.

The device has a plank connected to the base platform. The connection is such that the motion of the plank is limited to two axes and to two opposite directions on such axes. As such, the plank is rotatably secured relative to the base so as to provide four types of therapeutic ranges of motion. In one suitable implementation, the four types of motion consist of dorsiflexion and plantar flexion, eversion, and inversion.

To aid in dorsiflexion, the plank may include a strap located on the upper surface thereof and sized to receive the foot of the user in such strap.

In still other possible implementations, the connection between the plank and the base platform is made by means of a transversely oriented hinge, as well as a longitudinally oriented pivot, and two compressions springs. The transverse hinge is located on a rear segment of the plank and secured at the proximal end of the base platform. The pivot is connected to the plank so as to permit a forward segment of the plank to pivot about the longitudinal axis of the plank, either in a clockwise or counterclockwise direction relative to the base platform or relative to the rear segment.

In still further possible implementations, the ankle rehabilitation device has two forward corners on the forward segment of the plank. Two compressions springs are attached at their upper ends to such forward corners and at their lower ends are secured to the distal end portion of the base platform. The compression springs are adapted to permit rotation of the forward segment of the plank relative to the transverse hinge and adapted to exert linear opposing force, in response to sufficient foot force from dorsiflexion or plantar flexion of a foot received on the plank.

In certain implementations, the ankle rehabilitation device may be equipped with a foot rest which is moveably mounted to a base platform to selectively make available to the user one foot receiving portions on each side of the base platform. The foot rest is sized so that one of the user's feet can be received in either of the two foot receiving portions, while the other of the user's feet is received on the plank of the device. The foot rest is slidable by the user relative to the sides of the base platform between two positions. In this way, the foot rest, when engaged by one of the user's feet, secures the device from unintended movement while the other foot is moving on the plank.

One method of rehabilitating an ankle of a person's foot, according to this disclosure, involves receiving, on an upwardly facing surface, the foot associated with the ankle being rehabilitated. Movement of the surface is restricted to rotation in the clockwise or counterclockwise directions about two axes: a central longitudinal axis, rotation about which corresponds to eversion or inversion, and a transverse axis, rotation about which corresponds to dorsiflexion or plantar flexion.

In one variation of the method, the upwardly facing surface is placed at a desired location relative to the person, the desired location being proximate to the foot to be rehabilitated and received on the upwardly facing surface. A foot rest is in contact with the groundplane when the foot is received on the upwardly facing surface. The foot rest is selectively deployable adjacent opposite sides of the upwardly facing surface. As such, when the foot which is not being rehabilitated is placed on the foot rest, a holding force is transmitted to the upwardly facing surface to maintain the upwardly facing surface in the desired location, despite movements of such upwardly facing surface associated with rehabilitation.

These and other features of the foregoing inventions are further appreciated by reference to the following drawings, in which:

DESCRIPTION

Figure 1:
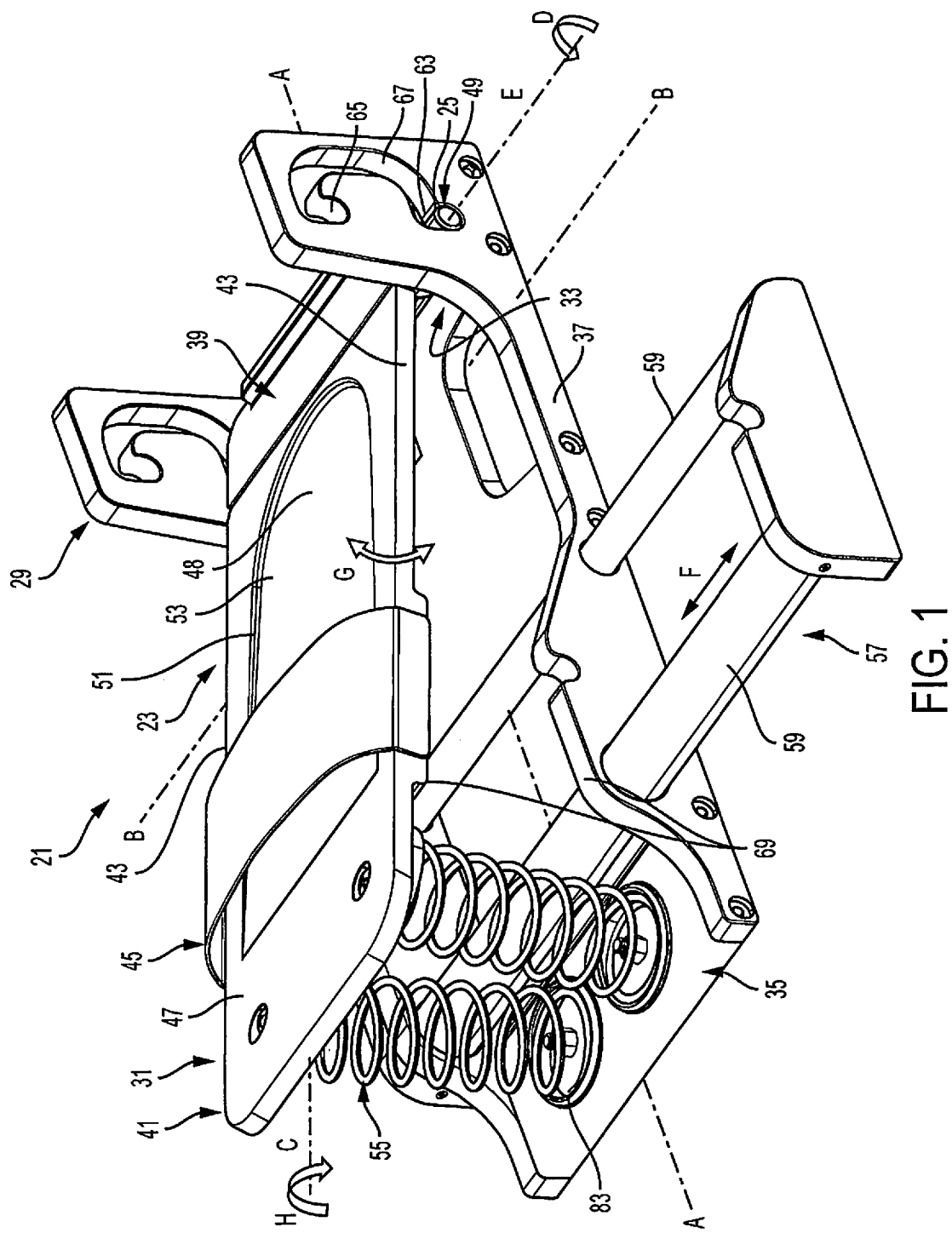
FIG. 1 is an isometric view showing one implementation of an ankle rehabilitation device according to the present disclosure.

Referring to FIGS. 1-6, one possible implementation of an ankle rehabilitation device 21 makes use of a plank 23 moveably secured to a base platform 29 at its proximal end so as to pivot about transverse hinge 25 in response to dorsiflexion or plantar flexion of a foot (not shown) received on upper surface 27 of plank 23. Plank 23 is further connected to base platform 29 at its forward or distal end 31 by two compression springs 55 extending between opposing surfaces of base platform 29 and plank 23. Plank 23 is configured in a manner described in more detail below so that it rotates clockwise or counterclockwise about two axes: a central longitudinal axis, in response to eversion and inversion of a foot received on plank 23; and a transverse axis, in response to dorsiflexion and plantar flexion.

The foregoing and other features to be described herein allow device 21 to isolate and exercise independently one or more muscle groups associated with certain ranges of foot/ankle motion as follows:

Plantar flexion: posterior and lateral muscles.

Dorsiflexion: Tibialis Anterior; Peroneus Tertius; Extensor Hallucis Longus; Extensor Digitorum Longus.

Inversion: Fibularis (Longus, Brevis, Tertius, Quartus); Anterior Tibialis; Extensor Digitorum Longus+Bervis, Extensor Hallucis Brevis.

Eversion: Peroneus Longus, Peroneus Brevis.

Device 21, although suitable for use in rehabilitation of the ankle, is equally suited for exercise, training and strengthening, and such uses are within the present disclosure. Accordingly, device 21 enables the user to stretch, increase strength, increase endurance, or increase AROM (Active Range of Motion) in the foot/ankle and its associated joints. It should be noted that the increase in strength possible with device 21 does not generally involve building muscle per se.

Having described certain general features of device 21 and their related uses above, further details of device 21 according to the illustrated implementation will now be described. Base platform 29 has a proximal end portion 33, and a distal end portion 35. A pair of opposite sides 37 extends between end portions 33, 35, and sides 37 are separated from each other by a corresponding base platform width. A longitudinal axis A extends between end portions 33, 35 and transverse axis B is defined perpendicular to longitudinal axis A.

Plank 23, in this implementation, comprises a rear segment 39 and a forward segment 41 extending distally from rear segment 39, as well as longitudinally extending plank sides 43, separated from each other to define an upper surface 47. Upper surface 47 has an area 48 defined on forward segment 41 and sized to receive the foot of the user thereon when the foot is placed on plank 23. Additionally, when foot is received on area 48, the forefoot may be engaged by strap 45 to maintain the foot proximate to upper surface 47.

Hinge 25 extends transversely across rear segment 39 of plank 23 and is secured at opposite hinge ends 49. In this way, plank 23 can be pressed downwardly or pulled upwardly by a foot received on area 48 of upper surface 47 of plank 23, in the two opposite directions shown by arrows G. As such, the user is able to rotate his or her foot up and down by applying force pressure downwardly or upwardly relative to plank 23, the down and up motions corresponding to plantar flexion or dorsiflexion, and the foot force required for such movements resulting in rehabilitation, strengthening or improving range of motion, as discussed above.

In the illustrated implementation, hinge 25 is in the form of a bar or barrel hinge, in which the two hinge ends 49 are rotatably connected at opposite sides 37 of base platform 29. In this manner, proximal end of plank 23 is limited to rotation in the direction D about transverse hinge axis E. Accordingly, muscles involved in plantar flexion or dorsiflexion are exercised by such rotation D about axis E, and by movement of plank 23 in the directions of arrows G. Securing hinge 25 at opposite ends 49 is one possible way to limit foot/ankle motion so as to isolate muscles involved in plantar flexion and dorsiflexion, thereby enhancing their rehabilitation.

In one suitable implementation, forward segment 41 includes a detent 51 forward of rear segment 39 of plank 23, such detent 51 forming a depression 53 adjacent detent 51, sized so that the heel of the foot placed on plank 23 may be received therein, thus forming a guide or heel print for the user to align the heel and rear portion of his or her foot and maintain the heel on forward segment 41 of plank 23.

Figure 6:
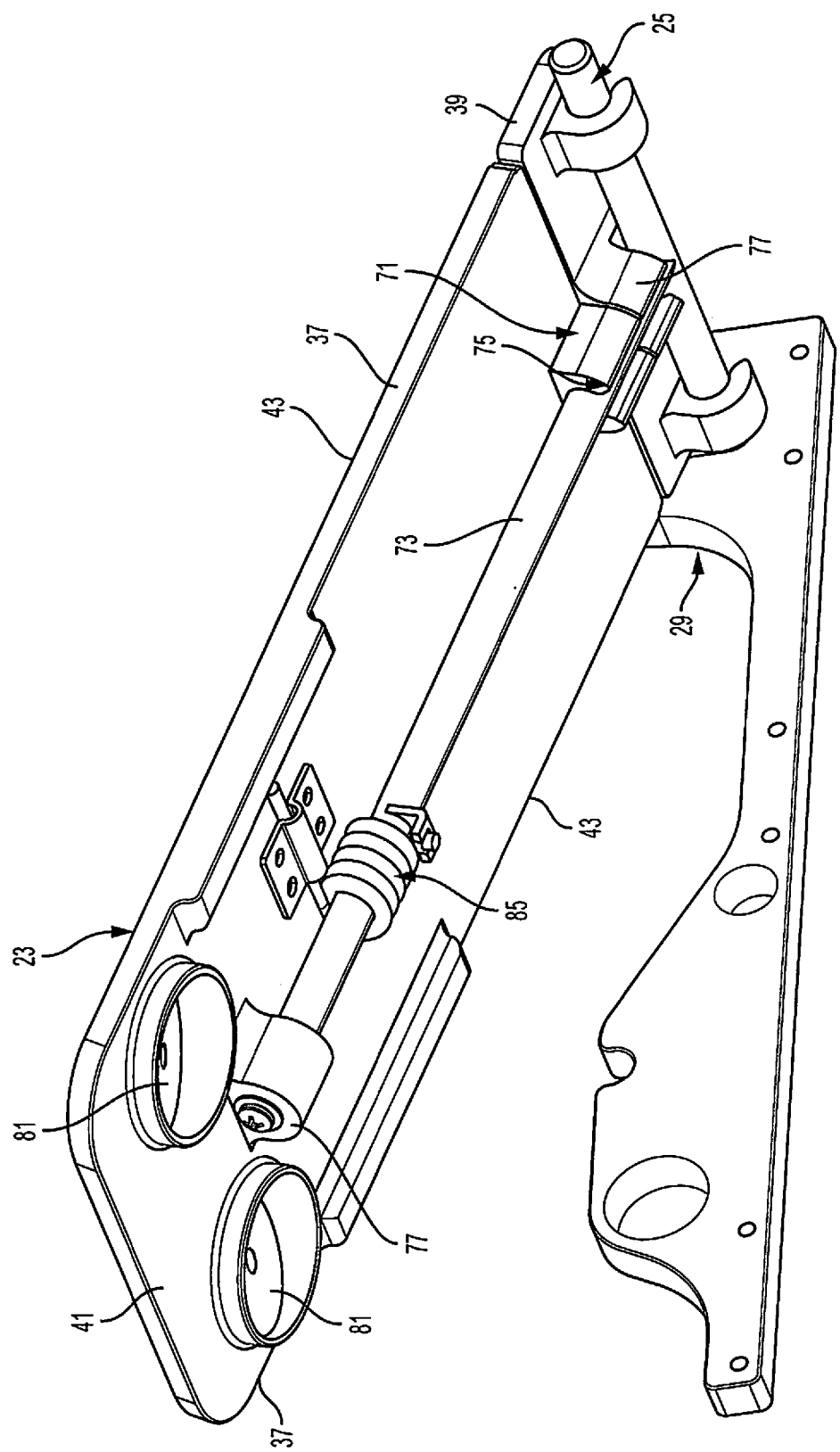
FIG. 6 is a partial isometric view showing portions of the base and plank of the implementation shown in FIGS. 1-5.

Forward segment 41 is moveably connected relative to rear segment 39 by means of a pivoting connection 71 (FIG. 6). Pivoting connection 71 is located and oriented to permit rotation of forward segment 41 in the directions of arrows H, in response to sufficient foot force on one lateral side of longitudinal axis C as compared to the other side. In this implementation, since rear segment 39 of plank 23 is limited to rotation about longitudinal axis C by virtue of hinge 25 having connection at hinge ends 49, placement of the foot within the heel print 53 assures that forward segment 41 may rotate in the directions of arrows H about longitudinal axis C, while rear segment 39 remains fixed relative thereto.

Figure 2:
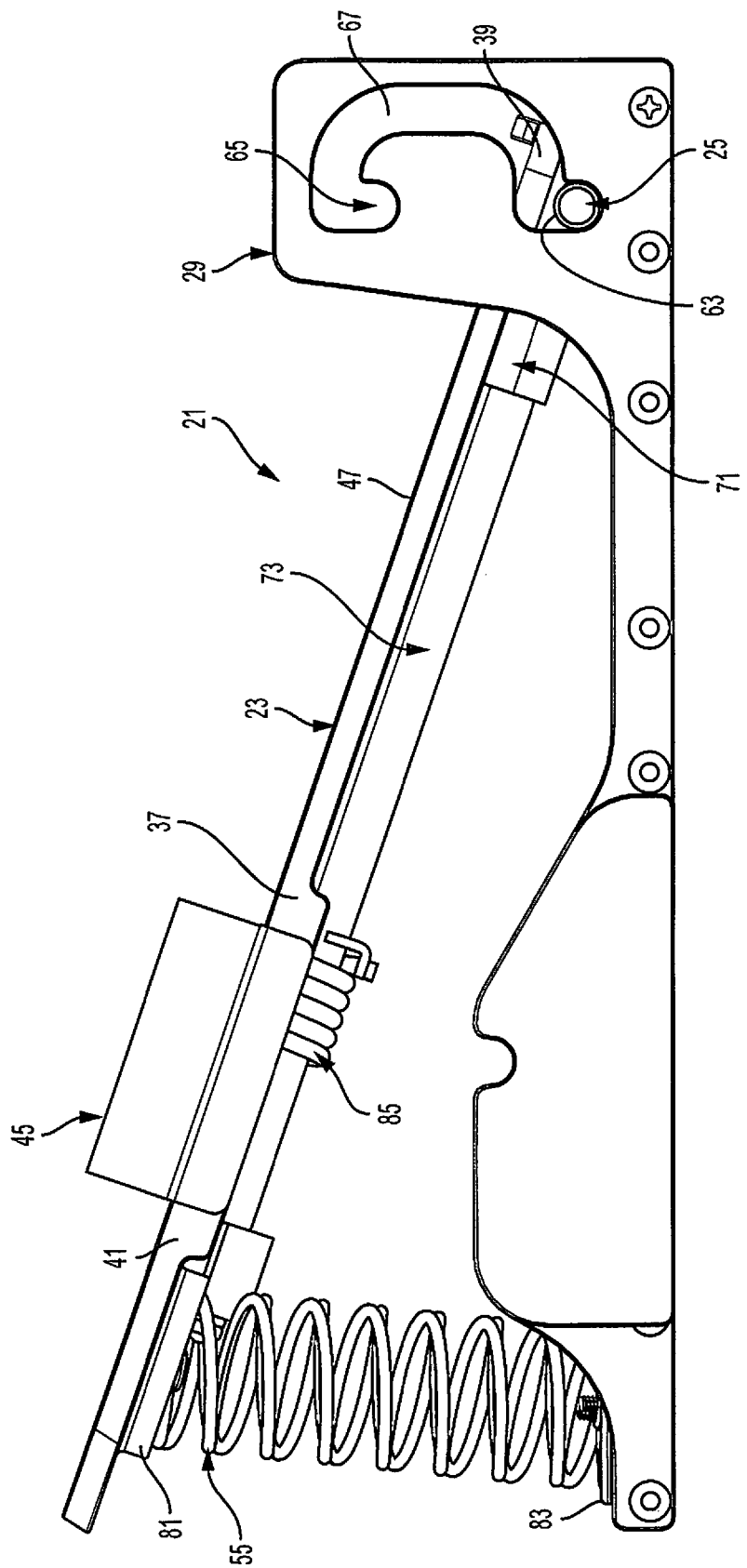
FIG. 2 is a side elevational view of the implementation shown in FIG. 1.
Figure 3:
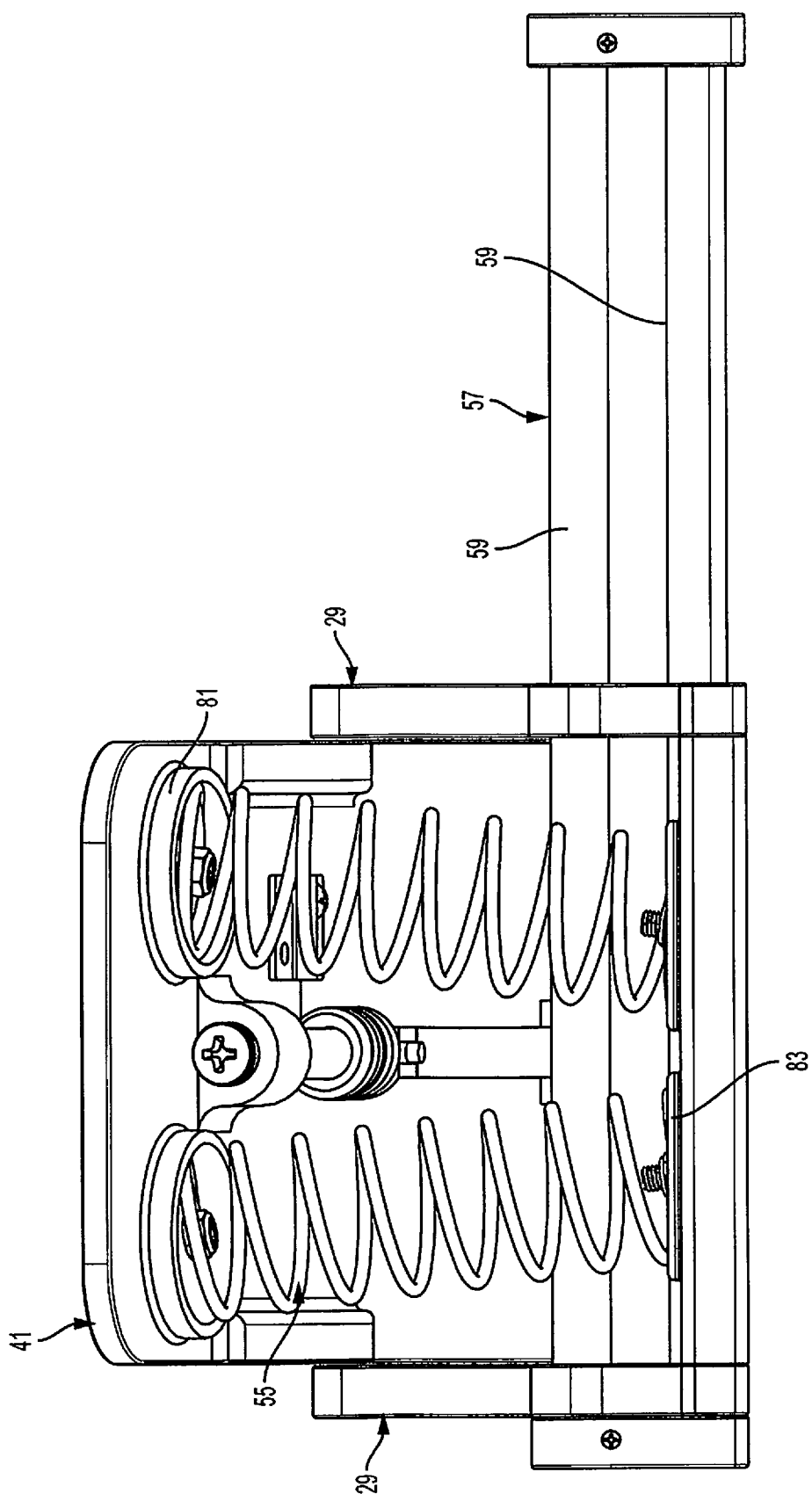
FIG. 3 is an elevational view of the implementation shown in FIGS. 1 and 2.
Figure 4:
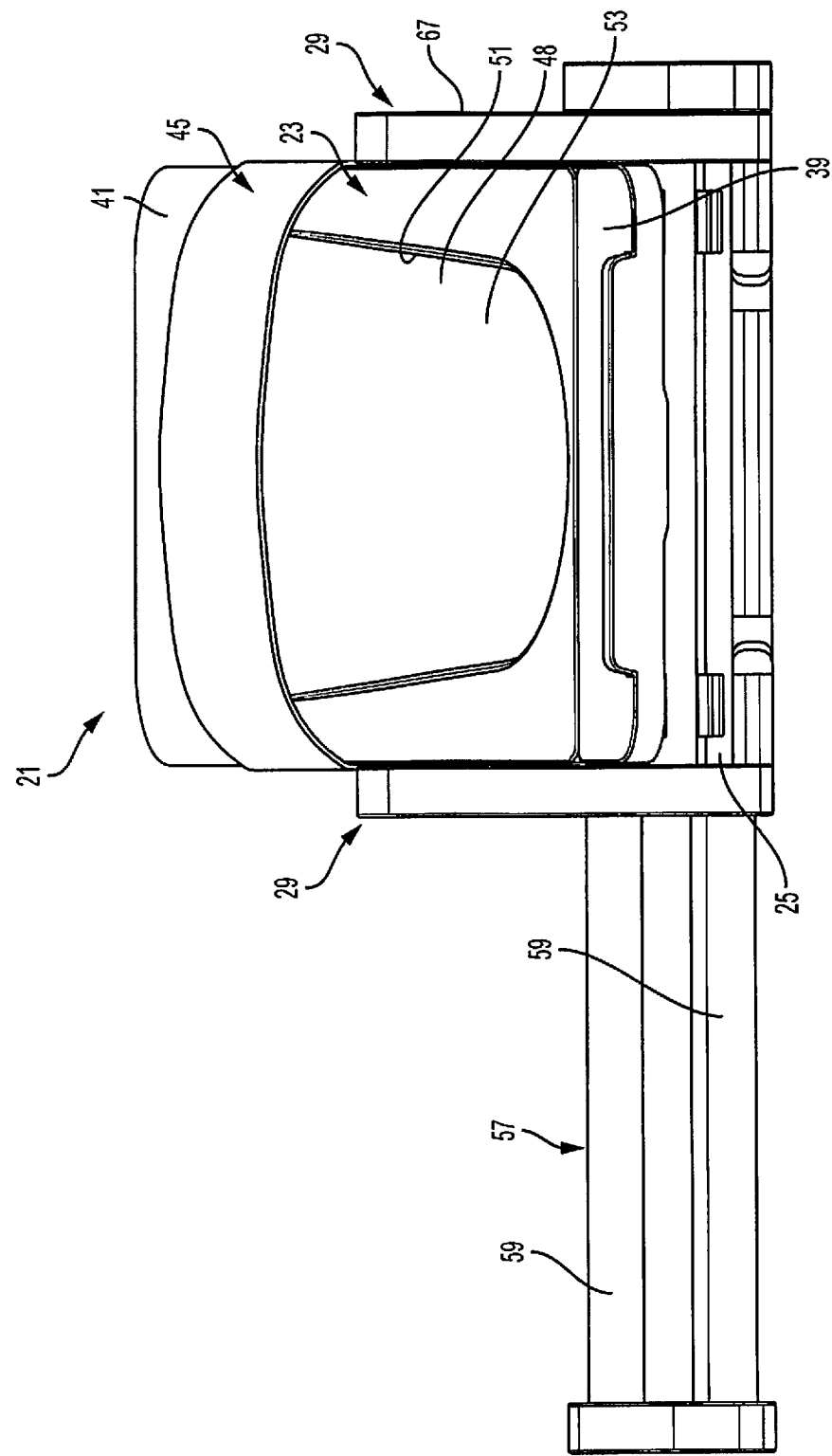
FIG. 4 is a front-elevational view of the implementation shown in FIGS. 1-3.
Figure 5:
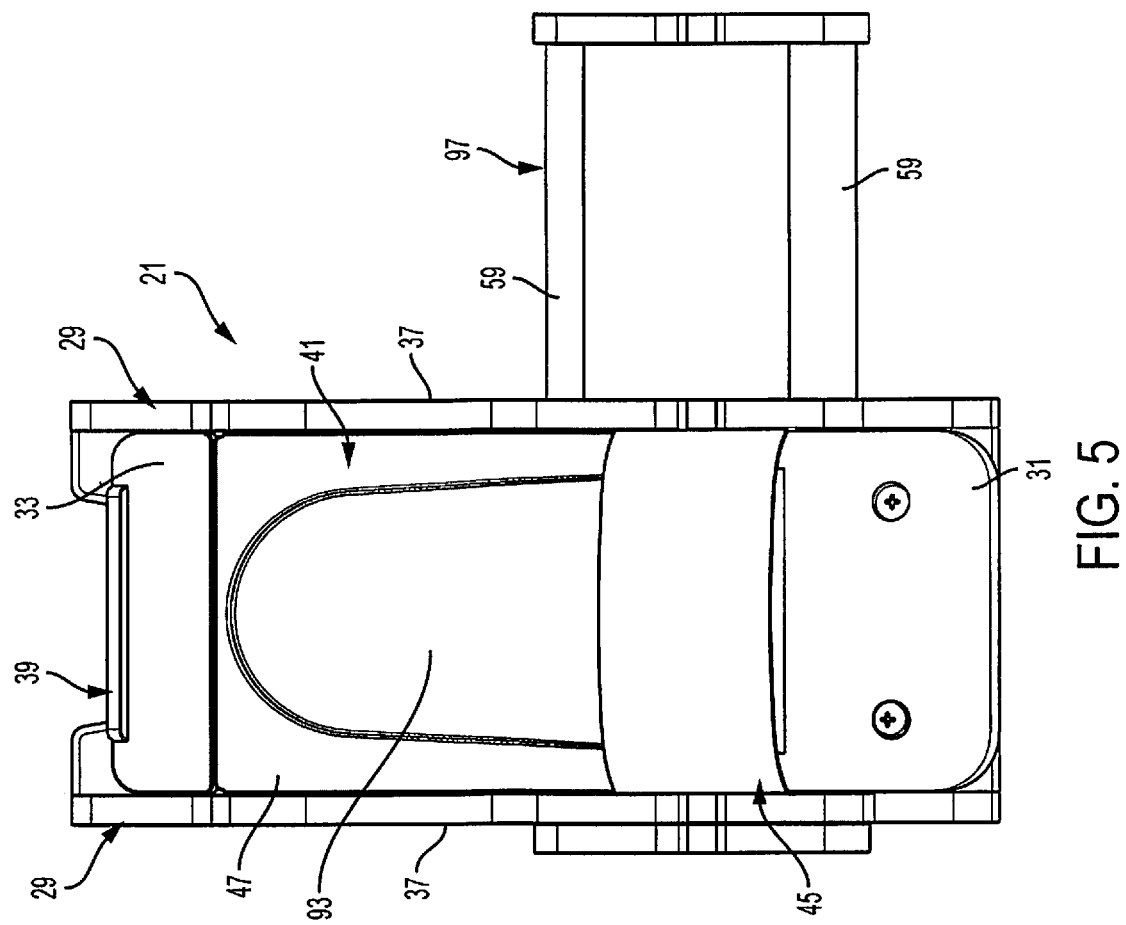
FIG. 5 is a top plan view of the implementation shown in FIGS. 1-4.

Pivot connection 71 may assume any number of suitable configurations to rotatably connect segments 39, 41 of plank 23 relative to each other. As best seen in FIGS. 2 and 6, forward segment 41 of plank 23 is rotatably secured at its proximal end relative to rear segment 39 by virtue of a longitudinally oriented pin 73. The implementation illustrated in FIG. 6 uses two flanges 75 mounted at spaced locations to the underside of forward segment 41 of plank 23. Pin 73 is aligned with longitudinal axis C of plank 23. Longitudinal axis C comprises the central longitudinal axis relative to sides 37 of plank 23. Pin 73 is rotatably received through respective apertures in flange 75. Pin 73 is fixably secured to bracket 77 at the forward or distal end of plank 23. Flanges 75 maintain pin 73 in its longitudinally aligned position relative to plank 23.

Plank 23 is connected to base platform 29 at its forward or distal end by a pair of compression springs 55. Compression springs 55 have upper ends secured to respective forward corners of plank 23, and lower ends secured to the distal end portion 35 of base platform 29. Compression springs 55 are selected so that, in response to user-initiated eversion and inversion, forward segment 41 of plank 23 may overcome the associated spring force and rotate, depending on the direction of the force, in either the directions of arrows H about central axis C, or, in response to dorsiflexion and plantar flexion, in the directions of arrows G relative to transverse hinge 25.

Furthermore, compression springs 55 maintain opposite sides 37 of plank 23 in substantial alignment with each other during rotation of plank 23 about hinge 25 during plantar flexion and dorsiflexion. As such, device 21 and plank 23 are capable of providing rehabilitative motion of eversion and inversion by rotation clockwise and counterclockwise in the directions of arrows G about longitudinal axis C, and dorsi-flexion and plantar flexion about axis E in arrow directions D. As explained above, the arrangement of connections between plank 23 and base platform 29, including compressions springs 55, is such that undesirable eversion and inversion of the user's foot does not occur during dorsiflexion and plantar flexion when plank 23 rotates about axis D of hinge 25, and such that undesirable flexion does not occur during eversion and inversion. Accordingly, the muscles associated with flexions and eversion/inversion, respectively, are substantially isolated and thereby more efficiently rehabilitated.

Compression springs 55 and other connection points between base platform 29 and plank 23 are also configured so that eversion and inversion is limited. For example, connections between plank 23 and base platform 29 may be configured to limit rotation about longitudinal axis C to an amount not exceeding 45 degrees of rotation clockwise or counterclockwise when measured relative to the at-rest position of plank 23 shown in the figures. The foregoing limitation may be accomplished by suitable selection of spring constants or other characteristics associated with compression springs 55, by selecting such springs to be of suitable length, and/or configuring plank 23 and base platform 29 with opposing surfaces 69 which are located relative to each other so that surfaces 69 come into contact when upper surface 47 of plank 23 is at the desired inclination, such as 45 degrees.

From a therapeutic standpoint, for certain foot/ankle conditions, it may be advantageous to have the proximal end of plank 23 in a more horizontal or more aligned position relative to its distal, forward end; whereas, in other situations, rehabilitation, therapy, or other exercises may be more advantageously accomplished by positioning the proximal end of plank 23 and its hinge 25 in a lower position vertically relative to base platform 29 and, presumably, the horizontal floor on which base platform 29 is generally placed. Accordingly, in certain applications, device 21 may benefit by configuring transversely oriented hinge 25, and corresponding transverse pivot point axis D for plank 23, to be moveable between two vertical positions. In this implementation, this is accomplished by providing base platform 29 with portions defining a serpentine channel 67 at each of the sides 37 of base platform 29. Channels 67 are sized and oriented to have corresponding hinge ends 49 slidably received in each such serpentine channel 67. A first lower notch 63 is formed at one end of serpentine channel 67, in this case a lower end relative to the ground plane, and a second notch 65 is formed at an upper end of serpentine channel 67. Notches 63, 65 are formed so that hinge ends 49, when received therein, are restrained from unintended movement during use. In this implementation, hinge ends 49 are generally located or urged to remain in notch 63 or 65 by encountering opposing wall portions of channels 67 when hinge ends 49 are received in notch 63, 65. In this way, the user can manually move the height of pivot axis D to a lower position corresponding to notches 63, or to an upper position corresponding to notches 65, with the expectation that hinge 25 will remain in the user-sedated position during use. In addition, the width or other construction characteristics of serpentine channels 67 may act to maintain hinge 49 in two different therapeutic positions when in use.

In the illustrated implementation, device 21 includes a foot rest 57, moveably mounted to base platform 29. Foot rest 57 has two foot receiving portions 59 sized to receive a corresponding one of the user's feet thereon. Foot rest 57 is slidable in the direction indicated by arrows F, transversely relative to sides 37 of base platform 29. In the illustrated embodiment, footrest 57 includes outside walls so that it can be slidable between two positions, one on either side of plank 23. In this way, a corresponding one of foot receiving portions 59 extends outwardly from a corresponding one of sides 37 of base platform 29. As such, the foot of the user which is not being received in plank 23 may be placed on the appropriate foot receiving portion 59 adjacent base platform 29.

Foot rest 55 may assume any number of configurations so that it is selectively deployable on opposite sides of base platform 29. In the illustrated implementation, foot rest 57 forms its foot receiving portions by means of a pair of transverse, elongated members, which are slidable through corresponding apertures in base platform 29.

As described herein, plank 23 is connected to base platform 29 by four connections in this implementation, namely, transversely oriented hinge 25, longitudinally oriented pivot connection 71, and the pair of compression springs 55 located at forward corners of plank 23. The foregoing connection arrangement is efficient in terms of cost and construction; provides four types of therapeutic ranges of motion (dorsiflexion, plantar flexion, eversion and inversion); provides such ranges of motion in isolation from one another; and, still further, avoids unwanted or extraneous rotations or movements of the foot, ankle, or calf while providing the desired aforesaid motions. Other connections and arrangements are likewise possible and within the scope of this disclosure.

In this illustrated implementation, compression springs 55 extend downwardly from plank 23 from respective engagement zones 81 on the undersurface of plank 23. Lower ends 83 of spring 55 are secured relative base platform 29. Compression springs 55 are in the form of linear springs. As such, compression springs 55 produce linear resistance or linear opposing force against rotation of plank 23 in direction of arrows H about longitudinal axis C, as well as rotation in the direction of arrows G. Such opposing forces are believed to provide therapeutic resistance to the four motions associated with device 21: eversion, inversion, dorsiflexion and plantar flexion. Although compression spring 55 are disclosed, equivalent means for providing device 21 with linear opposing force may be used and are within this disclosure; in addition, structures with parabolic resistance curves, cams, or other means to alter the linearity of the force-resistance curve may be suitable in certain applications of device 21.

So, for example, it may be desirable to increase opposition force to eversion and inversion occurring when plank 23 is rotated in the directions indicated by Arrows H. One suitable implementation to increase such opposing force is to provide torsional spring 85 operatively associated with plank 23 so that rotation of plank 23 relative to pin 73 encounters opposing spring force from torsional spring 85.

Compression springs 55 may be fixedly mounted at their opposing ends to opposing surfaces of plank 23 and base platform 29. In the illustrated implementation, compression springs 55 are removably attached at their ends so that they can be swapped out for other compression springs, or for other force resistant devices, materials and the like. So, by way of example and not limitation, a single one of devices 21 may be used for multiple users having therapeutic needs, by replacing one pair of compression springs 55, having certain characteristics, with another pair of compression springs having different characteristics. Accordingly, device 21 may include multiple pairs of the compression springs 55, each of the multiple pairs having different compression on other characteristics related to generation of opposing force. The different characteristics may be useful for different stages of rehabilitation of a single patient, for example, or for different patients with different strengths or other rehabilitation needs.

Having described implementations of the device herein, it would be appreciated that this disclosure is not limited to the precise details, methodologies, materials or geometries set forth herein, nor to particular constructions, shapes, and sizes of the various components of the features. Furthermore, this disclosure is not limited to the illustrated implementations or to variations thereof described herein. Accordingly, still further variations and implementations are within the spirit and scope of this disclosure.

What is claimed is:

1. An ankle rehabilitation device for use with either of a user's feet, the device comprising:
   a base platform having a proximal end portion and a distal end portion, a pair of opposite sides extending between the end portions and defining a base platform width, a longitudinal axis extending between the end portions, and a transverse axis defined perpendicular to the longitudinal axis;
   a plank having a rear segment and a forward segment, a plank longitudinal axis, and longitudinally extending plank sides, the forward segment of the plank sized to receive one of the user's feet thereon for rehabilitation, the plank having connections to the base platform to limit the plank to motion in two directions about two axes, to provide four types of therapeutic ranges of motion, comprising dorsiflexion plantar flexion, eversion, and inversion;
   wherein the plank comprises a strap located on upper surface of the plank and sized to receive the foot of the user received on the plank;
   wherein the connections of the plank to the base platform comprise a transversely oriented hinge, a longitudinally oriented pivot, and two compression springs;
   wherein the hinge is located on the rear segment of the plank and secured to the proximal end portion of the base platform;
   wherein the pivot is connected to the plank to permit the forward segment to pivot about the plank longitudinal axis either clockwise or counterclockwise relative to the rear segment in response to sufficient increased foot force on one of the sides of the forward segment of the plank relative to the force on the other of the sides;
   wherein the forward segment of the plank has two forward corners, and wherein the two compression springs have upper ends secured to respective forward corners of the plank, the compression springs having lower ends secured to the distal end portion of the base platform;
   wherein the compression springs are adapted to permit rotation of the forward segment of the plank relative to the hinge and to exert linear opposing force in response to sufficient increased foot force from plantar and dorsiflexion; and
   a foot rest movably mounted to the base platform, the foot rest having two foot-receiving portions sized to receive one of the user's feet thereon, the foot rest transversely slidable by the user relative to the sides of the base platform between two positions, the foot rest having a foot rest width greater than the width of the base platform, wherein, in each of the two slidable positions, a corresponding one of the foot-receiving portions extends outwardly from a corresponding side of the base platform, whereby the foot of the user not being rehabilitated may be placed adjacent the base platform.

2. The device of claim 1, wherein, in response to human-induced foot force, the connections between the plank and the base platform are adapted to permit rotation about the longitudinal plank axis up to but not exceeding 45 degrees rotation clockwise or counterclockwise.

3. The device of claim 1, wherein the hinge is moveable vertically relative to the base platform.

4. The device of claim 3, wherein the hinge is moveable vertically between upper and lower positions relative to a bottom plane of the base platform.

5. The device of claim 1, wherein the hinge comprises a pin received in corresponding apertures defined on the sides of the base platform.

6. The device of claim 1, wherein the connections between the plank and the base platform consist of the transversely oriented hinge, the longitudinally oriented pivot connection, and the two compression springs.

7. The device of claim 1, wherein the two compression springs extend at respective angles relative to vertical, thereby opposing rotational force from rotation about the plank longitudinal axis.

8. The device of claim 1, wherein the plank longitudinal axis comprises a central longitudinal axis bisecting the forward segment of the plank.

9. The device of claim 1, wherein the compression springs are removably replaceable, and further comprising multiple pairs of the compression springs, each of the multiple pairs having different compression characteristics, whereby a single device may be used by multiple users having different therapeutic needs.

10. The device of claim 1, wherein the foot rest comprises a pair of transverse elongated members slidable through at least one corresponding aperture in the base platform.

11. An ankle rehabilitation device for use with either of a user's feet, the device comprising: a base platform having a proximal end portion and a distal end portion, a pair of opposite sides extending between the end portions and defining a base platform width, a longitudinal axis extending between the end portions; and a transverse axis defined perpendicular to the longitudinal axis;
   a plank having a rear segment and a forward segment, a plank longitudinal axis, and longitudinally extending plank sides, the forward segment of the plank sized to receive one of the user's feet thereon for rehabilitation, the plank having connections to the base platform to limit the plank to motion in two directions about two axes, to provide four types of therapeutic ranges of motion, comprising dorsiflexion and plantar flexion, eversion, and inversion;
   wherein the plank comprises a strap located on upper surface of the plank and sized to receive the foot of the user received on the plank;
   wherein the connections between the plank and the base platform consist of a transversely oriented hinge, a longitudinally oriented pivot connection, and two compression springs;
   wherein the hinge is located on the rear segment of the plank and secured to the proximal end portion of the base platform;
   wherein the pivot is connected to the plank to permit the forward segment to pivot about the plank longitudinal axis either clockwise or counterclockwise relative to the rear segment in response to sufficient increased foot force on one of the sides of the forward segment of the plank relative to the force on the other of the sides;
   wherein the forward segment of the plank has two forward corners, and wherein the two compression springs have upper ends secured to respective forward corners of the plank, the compression springs having lower ends secured to the distal end portion of the base platform;
   wherein the compression springs are adapted to permit rotation of the forward segment of the plank relative to the hinge and to exert linear opposing force in response to sufficient increased foot force from plantar and dorsiflexion;
   a foot rest movably mounted to the base platform, the foot rest having two foot-receiving portions sized to receive one of the user's feet thereon, the foot rest transversely slidable by the user relative to the sides of the base platform between two positions, the foot rest having a foot rest width greater than the width of the base platform, wherein, in each of the two slidable positions, a corresponding one of the foot-receiving portions extends outwardly from a corresponding side of the base platform, whereby the foot of the user not being rehabilitated may be placed adjacent the base platform;

wherein the compression springs are removably replaceable, and further comprising multiple pairs of the compression springs, each of the multiple pairs having different compression characteristics, whereby a single device may be used by multiple users having different therapeutic needs.

12. The device of claim 11, wherein, in response to human-induced foot force, the connections between the plank and the base platform are adapted to permit rotation about the longitudinal plank axis up to but not exceeding 45 degrees rotation clockwise or counterclockwise.

13. The device of claim 1, wherein the hinge is moveable vertically relative to the base platform.

14. The device of claim 13, wherein the hinge is moveable vertically between upper and lower positions relative to a bottom plane of the base platform.

15. The device of claim 1, wherein the hinge comprises a pin received in corresponding apertures defined on the sides of the base platform.

16. A method of rehabilitating an ankle of a person's foot, the method comprising:

providing an ankle rehabilitation device according to claim 1;

receiving, on an upwardly facing surface of the plank, the foot associated with the ankle being rehabilitated, the surface being movable relative to a ground plane;

restricting movement of the plank to rotation in the clockwise or counterclockwise directions about two axes, wherein:

one of the axes comprises the plank longitudinal axis, wherein the plank longitudinal axis is centrally located relative to the width of the plank and the rotation about the plank longitudinal axis corresponds to eversion or inversion; and wherein the other of the axes comprises the transverse axis, and the rotation about the transverse axis corresponds to dorsiflexion or plantar flexion.

17. The method of claim 16, further comprising the step of restricting separation of the bottom of the foot from the upwardly facing surface when the foot has been received on the upwardly facing surface.

18. The method of claim 16, further comprising exerting corresponding linear opposing forces to movements of the foot received on the surface relative to the ground plane.

19. The method of claim 16, further comprising manually moving the location of the transverse axis relative to the ground plane between two predetermined heights.

20. The method of claim 16, further comprising:

placing the upwardly facing surface at a desired location relative to the person, the desired location being proximate to the foot to be rehabilitated and received on the upwardly facing surface;

associating the upwardly facing surface with a foot rest in contact with the groundplane when the foot is received on the upwardly facing surface, the foot rest being selectively deployable adjacent opposite sides of the upwardly facing surface; and receiving the foot not being rehabilitated on the foot rest to transmit holding force to the upwardly facing surface to maintain the upwardly facing surface in the desired location.

* * * * *